(12) United States Patent
Owen

(10) Patent No.: US 9,188,555 B2
(45) Date of Patent: Nov. 17, 2015

(54) AUTOMATED EDS STANDARDS CALIBRATION

(75) Inventor: Michael James Owen, Geebung (AU)

(73) Assignee: FEI Company, Hillsboro, OR (US)

( * ) Notice: Subject to any disclaimer, the term of this patent is extended or adjusted under 35 U.S.C. 154(b) by 622 days.

(21) Appl. No.: 13/561,821

(22) Filed: Jul. 30, 2012

(65) Prior Publication Data

US 2014/0032131 A1    Jan. 30, 2014

(51) Int. Cl.
    *G01N 23/225*    (2006.01)
    *G01N 31/20*    (2006.01)
    *G06F 17/10*    (2006.01)
    *G01N 33/28*    (2006.01)

(52) U.S. Cl.
CPC ............ *G01N 23/2252* (2013.01); *G06F 17/10* (2013.01); *G01N 33/2823* (2013.01); *G01N 2223/3037* (2013.01); *G01N 2223/616* (2013.01)

(58) Field of Classification Search
CPC ................ G01N 2223/3037; G01N 2223/616; G01N 23/2252; G01N 33/2823; G05F 17/10
USPC .............. 702/28, 40, 134; 250/305, 307, 310, 250/339.09; 356/326; 850/10
See application file for complete search history.

(56) References Cited

U.S. PATENT DOCUMENTS

| | | | |
|---|---|---|---|
| 4,037,101 A | 7/1977 | Okumura et al. | |
| 4,136,429 A | 1/1979 | Brandes | |
| 4,242,586 A | 12/1980 | Warble | |
| 4,435,507 A | 3/1984 | Stenkvist | |
| 4,476,386 A | 10/1984 | Reid et al. | |
| 4,587,424 A | 5/1986 | Grau | |
| 4,592,082 A | 5/1986 | Pawloski | |

(Continued)

FOREIGN PATENT DOCUMENTS

| | | |
|---|---|---|
| CN | 100498309 | 6/2009 |
| JP | 05087707 | 4/1993 |

(Continued)

OTHER PUBLICATIONS

Ashton, Edward A., "Multialgorithm solution for automated multispectral target detection," Opt. Eng., Apr. 1999, pp. 717-724, vol. 38, No. 4.

(Continued)

*Primary Examiner* — John H Le
(74) *Attorney, Agent, or Firm* — Scheinberg & Associates, PC; Michael O. Scheinberg; John B. Kelly

(57) ABSTRACT

This invention relates to a method and system for determining the composition of an unknown sample. The present invention is directed to a method of calibrating an x-ray spectrometer that does not require measuring all possible elements under the operating conditions used to measure the unknown sample to be analyzed. According to a preferred embodiment, the local instrument can be calibrated from an x-ray spectrum of a single elemental standard. The instrument will have a stored library containing high quality spectra for all elements being analyzed. The analysis of the single element is compared to the library spectra for that element to define a transformation that is used to create a calibrated spectra library that includes a calibrated spectrum for each spectrum in the original library. The spectra generated by the local instrument can be compared to the calibrated library spectra to determine the elements in an unknown mineral.

20 Claims, 3 Drawing Sheets

(56) References Cited

U.S. PATENT DOCUMENTS

| | | |
|---|---|---|
| 4,807,148 A | 2/1989 | Lacey |
| 4,834,943 A | 5/1989 | Yoshiyama |
| 4,839,516 A | 6/1989 | Freeman et al. |
| 5,084,618 A | 1/1992 | Ito |
| 5,475,220 A * | 12/1995 | Hughes et al. ........... 250/339.09 |
| 5,555,198 A | 9/1996 | Asano |
| RE35,514 E | 5/1997 | Albrecht et al. |
| 5,741,707 A | 4/1998 | Herron et al. |
| 5,798,525 A | 8/1998 | Benizri-Carl et al. |
| 5,866,903 A | 2/1999 | Morita et al. |
| 5,906,919 A | 5/1999 | Garini et al. |
| 5,991,028 A | 11/1999 | Cabib et al. |
| 6,018,587 A | 1/2000 | Cabib |
| 6,066,459 A | 5/2000 | Garini et al. |
| 6,072,178 A | 6/2000 | Mizuno |
| 6,093,930 A | 7/2000 | Boyette, Jr. et al. |
| 6,122,343 A | 9/2000 | Pidcock |
| 6,140,643 A * | 10/2000 | Brown et al. .................... 850/10 |
| 6,282,301 B1 | 8/2001 | Haskett |
| 6,341,257 B1 | 1/2002 | Haaland |
| 6,377,652 B1 | 4/2002 | Sturm |
| 6,466,929 B1 | 10/2002 | Brown et al. |
| 6,470,335 B1 | 10/2002 | Marusak |
| 6,584,413 B1 | 6/2003 | Keenan et al. |
| 6,658,143 B2 | 12/2003 | Hansen et al. |
| 6,674,894 B1 | 1/2004 | Parker et al. |
| 6,687,620 B1 | 2/2004 | Haaland et al. |
| 6,711,503 B2 | 3/2004 | Haaland |
| 6,723,871 B2 | 4/2004 | Tada et al. |
| 6,724,940 B1 | 4/2004 | Qian et al. |
| 6,765,205 B2 | 7/2004 | Ochiai et al. |
| 6,842,702 B2 | 1/2005 | Haaland et al. |
| 6,888,920 B2 | 5/2005 | Blank et al. |
| 6,977,723 B2 | 12/2005 | Lemmo et al. |
| 6,993,170 B2 | 1/2006 | Johnson et al. |
| 7,053,365 B2 | 5/2006 | Shimomura |
| 7,061,605 B2 | 6/2006 | Lemmo et al. |
| 7,108,970 B2 | 9/2006 | Levinson |
| 7,132,652 B1 | 11/2006 | Testoni |
| 7,139,415 B2 | 11/2006 | Finkbeiner |
| 7,161,672 B2 | 1/2007 | Gornushkin et al. |
| 7,243,030 B2 | 7/2007 | Reeve et al. |
| 7,400,770 B2 | 7/2008 | Keaton et al. |
| 7,436,510 B2 | 10/2008 | Grun et al. |
| 7,456,399 B1 | 11/2008 | Soderstrom |
| 7,490,009 B2 | 2/2009 | Gottlieb et al. |
| 7,790,465 B2 | 9/2010 | Otvos |
| 7,804,059 B2 | 9/2010 | Harrison |
| 7,930,106 B2 | 4/2011 | Carrick |
| 7,979,217 B2 | 7/2011 | Gottlieb et al. |
| 8,060,173 B2 | 11/2011 | Goode, Jr. et al. |
| 8,119,991 B2 | 2/2012 | Harrison |
| 2002/0169589 A1 | 11/2002 | Banki et al. |
| 2004/0011958 A1 | 1/2004 | Wright et al. |
| 2004/0027350 A1 | 2/2004 | Kincaid et al. |
| 2004/0099805 A1 | 5/2004 | Ochiai et al. |
| 2004/0147830 A1 | 7/2004 | Parker et al. |
| 2005/0037515 A1 | 2/2005 | Nicholson et al. |
| 2005/0060868 A1 | 3/2005 | McMurtry |
| 2005/0165290 A1 | 7/2005 | Kotsianti et al. |
| 2006/0051251 A1 | 3/2006 | Desrosiers et al. |
| 2006/0291619 A1 | 12/2006 | Statham |
| 2007/0181793 A1 | 8/2007 | Harrison |
| 2007/0279629 A1 | 12/2007 | Grun et al. |
| 2008/0137082 A1 | 6/2008 | Grun et al. |
| 2008/0250881 A1 | 10/2008 | Dona |
| 2009/0296086 A1 * | 12/2009 | Appel et al. .................. 356/326 |
| 2010/0060893 A1 | 3/2010 | Norton et al. |
| 2011/0144922 A1 | 6/2011 | Corbett et al. |
| 2011/0155907 A1 | 6/2011 | Bushell |
| 2011/0301869 A1 | 12/2011 | Gottlieb et al. |
| 2013/0015351 A1 | 1/2013 | Kooijman et al. |
| 2013/0134307 A1 | 5/2013 | Routh, Jr. |

FOREIGN PATENT DOCUMENTS

| | | |
|---|---|---|
| JP | 08015185 | 1/1996 |
| JP | 10312763 | 11/1998 |
| JP | 2000249668 | 9/2000 |
| JP | 2001006597 | 1/2001 |
| JP | 2001066269 | 3/2001 |
| JP | 2002189005 | 7/2002 |
| JP | 2005274352 | 10/2005 |
| JP | 2011113640 | 6/2011 |
| RU | 2054660 | 2/1996 |
| WO | 9905503 | 2/1999 |
| WO | 2008013597 | 1/2008 |
| WO | 2009100404 | 8/2009 |

OTHER PUBLICATIONS

Benz, Ursula C., et al., "Multi-resolution, object-oriented fuzzy analysis of remote sensing data for GIS-ready information," ISPRS Journal of Photogrammetry & Remote Sensing, 2004, pp. 239-258, vol. 58.

Creelman, Robert A., et al., "A scanning electron microscope method for automated, quantitative analysis of mineral matter in coal," International Journal of Coal Geology, 1996, pp. 249-269, vol. 30.

Unknown, "Energy-dispersive X-ray spectroscopy," Wikepedia, http://en.wikipedia.org/wiki/Engergy_Dispersive_Spectroscopy, obtained Jul., 29, 2013, 3 pages.

Fandrich, Rolf, et al., "Modern SEM-based mineral liberation analysis," Int. J. Miner. Process., 2007, pp. 310-320, vol. 84.

Figueroa, German, et al., "Advanced Discrimination of Hematite and Magnetite by Automated Mineralogy," 10th ICAM, Aug. 1-5, 2011, pp. 197-204.

Furse, J.E., "Kinematic design of fine mechanisms in instruments," J. Phys. E: Sci. Instrum, 1981, pp. 264-272, vol. 14.

Ghassemian, Hassan, et al, "Object-Oriented Feature Extraction Method for Image Data Compaction," IEEE Control Systems Magazine, Jun. 1998, pp. 42-48.

Gottlieb, P., et al., "The Automatic Identification and Quantification of Silver Minerals," XVIII International Mineral Processing Congress, May 23-28, 1993, pp. 475-481.

Gottlieb, P. et al., "Using Quantitative Electron Microscopy for Process Mineralogy Applications," JOM, Apr. 2000, pp. 24-25.

Gu, Ying, "Automated Scanning Electron Microscope Based Mineral Liberation Analysis, An Introduction to JKMRC/FEI Mineral Liberation Analyser," Journal of Mineral & Materials Characterization & Engineering, 2003, pp. 33-41, vol. 2, No. 1.

Hale, Layton C., et al., "Optimal design techniques for kinematic couplings," Journal of the International Societies for Precision Engineering and Nanotechnology, 2001, pp. 114-127, vol. 25.

Hazel, Geoffrey G., "Object-level Processing of Spectral Imagery for Detection of Targets and Changes Using Spatial-Spectral-Temporal Techniques," Proceeding of the SPIE, 2001, pp. 380-390, vol. 4381.

Jana, Dipayan, "Sample Preparation Techniques in Petrographic Examinations of Construction Materials: A State-Of the-Art Review," Proceedings of the twenty-eighth Conference on Cement Microscopy, Apr. 30-May 4, 2006, 48 pages.

Lapicki, Adam, et al., "Kinematic sample mounting system for accurate positioning of transferrable samples," J. Vac. Sci. Technol. A, Sep./Oct. 2000, pp. 2603-2605, vol. 18 No. 5.

Meyer, K., et al., "Qualitative and quantitative mixture analysis by library search: infrared analysis of mixtures of carbohydrates," Analytica Chimica Acta, 1993, pp. 161-171, vol. 281.

Newbury, Dale E., "Chemical compositional mapping by microbeam analysis at the micrometer scale and finer," Microelectronics Journal, 1997. pp. 489-508, vol. 28.

Newbury, Dale "Pushing the Envelope with SEM/SDD-EDS Mapping: X-ray Spectrum Image Mapping in 30 Seconds or Less, But What are the Real Limits?" Proc. of SPIE, 2010, 9 pages, vol. 7729.

Oversluizen, Tom, et al., "Kinematic mounting systems for National Synchrotron Light Source beamlines and experiments," Rev. Sci. Instrum., Jan. 1992, pp. 1285-1288, vol. 63 No. 1.

Pirrie, Duncan, et al., "Rapid quantitative mineral and phase analysis using automated scanning electron microscopy (QemSCAN); poten-

(56) References Cited

OTHER PUBLICATIONS tial applications in forensic geoscience," Forensic Geoscience: Principles, Techniques and Applications, 2004, pp. 123-136.

Pye, Kenneth, et al., "Forensic Geoscience: Principles, Techniques and Applications," The Geological Society, Mar. 3 & 4, 2003, 55 pages.

Pye, Kenneth, et al., "Forensic Geoscience: Principles, Techniques and Applications," The Geological Society, 2004, 25 pages.

Slocum, A. H., "Kinematic couplings for precision fixturing—Part I: Formulation of design parameters," Precision Engineering, Apr. 1988, pp. 85-92, vol. 10 No. 2.

Slocum, A. H., et al., "Kinematic couplings for precision fixturing—Part 2: Experimental determination of repeatability and stiffness," Precision Engineering, Jul. 1988, pp. 115-122, vol. 10 No. 3.

Slocum, Alexander H., "Design of three-groove kinematic couplings," Precision Engineering, Apr. 1992, pp. 67-77, vol. 14, No. 2.

Slocum, Alexander, "Kinematic couplings: a review of design principles and applications," International Journal of Machine Tools & Manufacture, 2010, pp. 310-327, vol. 50.

Sutherland, D. N., et al., "Application of Automated Quantitative Mineralogy in Mineral Processing," Minerals Engineering, 1991, pp. 753-762, vol. 4 No. 7-11.

Sutherland, D. N., "Image Analysis for Off-Line Characterisation of Mineral Particles and Prediction of Processing Properties," Part. Part. Syst. Charact., 1993, pp. 271-274, vol. 10.

Unknown, "Raith e_Line User Guide," online, Nov. 2009, 18 pages.

Van Hoek, Corrie J.G., et al., "A SEM-EDS Study of Cultural Heritage Objects with Interpretation of Constituents and Their Distribution Using PARC Data Analysis," Microsc. Microanal. 2011, pp. 656-660, vol. 17.

Zelenika, S., et al., "Kinematic Couplings for Synchrotron Radiation Instrumentation," 2nd International Workshop on Mechanical Engineering Design of Synchrotron Radiation Equipment and Instrumentation, Sep. 5-6, 2002, 9 pages.

* cited by examiner

AUTOMATED EDS STANDARDS CALIBRATION

TECHNICAL FIELD OF THE INVENTION

The present invention relates generally to methods and structures for identifying minerals using charged particle beam systems and energy dispersive spectroscopy systems.

BACKGROUND OF THE INVENTION

Mineral analysis systems, such as the QEMSCAN® (Quantitative Evaluation of Minerals by Scanning electron microscopy) and MLA (Mineral Liberation Analyzer) from FEI Company, the assignee of the present invention, have been used for many years to determine the presence of valuable minerals in mines. Such systems direct an electron beam toward the sample and measure the energy of x-rays coming from the material in response to the electron beam. One such process is called "energy dispersive x-ray analysis" or "EDS," which can be used for elemental analysis or chemical characterization of a sample. Determining the elements present in a mineral sample is referred to as "elemental decomposition."

EDS systems rely on the emission of x-rays from a sample to perform elemental analysis. Each element has a unique atomic structure, so x-rays that are characteristic of an element's atomic structure are unique to that element. To stimulate the emission of x-rays from a sample, a beam of charged particles is focused onto the sample, which causes electrons from inner shells to be ejected. Electrons from outer shells seek to fill this electron void, and the difference in energy between the higher energy shell and the lower energy shell is released as an x-ray, which can be detected by an EDS detector.

By measuring the number and energy of the x-rays emitted from a specimen using an energy-dispersive spectrometer and comparing the measured spectra to a library of reference spectra of known compositions, the unknown elemental composition of the specimen can be determined. EDS analysis, especially when coupled with back-scattered electron (BSE) analysis, can be used to quantify a wide range of mineral characteristics, such as mineral abundance, grain size, and liberation, that is, how easy it is to separate a desired mineral from background materials. Existing EDS analysis systems include QEM*SEM technology, which is assigned to FEI Company, Inc, the assignee of the present invention.

A mineral classification system must be capable of comparing each unknown measured spectrum to a library of known mineral spectrums, and then making a selection based on which known mineral is most similar to the measured spectrum. Typically, to find the most similar spectrum requires the use of a metric that represents the degree of similarity between the measured data and the known material.

Mineral analysis systems of this type are also used in the oil and gas industry. Drill cuttings (drill bit-induced rock chips) and diamond drill cores can be analyzed to allow geologists to determine the exact nature of the material encountered during drilling, which in turn allows more accurate predictions as to the material still ahead of the drill, thus reducing risk in exploration and production. During drilling, a liquid referred to as "mud" is injected into the well to lubricate the drill and return the cuttings out of the well. A sample can be taken from the mud that includes cuttings from the drill. Documenting cuttings and cores as accurately as possible, both at the time of drilling and post-drilling, is an important facet of analyzing the drilling process. The information obtained from cutting and coring samples allows characterization of down-hole lithological variation in a reservoir sequence, a critical requirement in exploration and production wells, and mineralogical and petrographic studies underpin the fundamental understanding of reservoir and seal characteristics. Traditional optical, scanning electron microscope (SEM), electron probe micro-analyzer (EPMA) and x-ray diffraction (XRD) analysis methods are well established and widely used within the industry.

Mineral analysis attempts to identify the minerals present and their relative proportions at any point to which the electron beam is directed. An analysis instrument typically measures an x-ray signal, determines what elements are present, and then translates that list of elements into a mineral identification using a database of mineral definitions.

A particular mineral always has peaks at certain energies in the x-ray spectrum. To accurately determine which peaks correspond to which minerals, it is necessary to calibrate the instrument being utilized before it can identify the unknown minerals. For this reason, instrument calibration techniques are particularly important for meaningful analysis.

An EDS instrument is typically calibrated using either a standards-based calibration or a standards-less calibration. In standards-based calibration, known materials, referred to as "standards," are analyzed and the results are used to establish a spectra library. Unknown samples are then compared to the calibration database to determine what elements are present. The spectrum of the calibration standards must be obtained under identical conditions as the conditions used to obtain the spectrum of the unknown material. Because conditions in the measuring instrument depend on a number of factors, conventional standards-based calibration requires measurement of the full set of standards each day when the machine is used. For example, the QemScan instrument described above currently identifies a maximum of 72 different elements found in mineral samples. Conventional standards-based calibration would require that each instrument have a set of 72 elemental/mineral standards to generate a full set of x-ray spectra for the decomposition. This type of calibration is prohibitively expensive, both in terms of the cost to supply a standard block containing the full set of elemental and mineral standards, and in terms of the operator time required and reduced instrument through-put. In addition, as there are several elements that only exist in minerals and can't be measured individually, it is not possible to perform this calibration for those elements.

Factory calibration using prior art methods is not practical because conventional standards-based decomposition requires that the x-ray spectra of all the elemental standards be acquired on the same machine under the same conditions as the x-ray spectrum of the mineral being analyzed. Prior art suggests that standards based elemental analysis requires that the elemental x-ray spectra need to be measured on the same machine and cannot be taken from another machine. This is because variations in the way a user sets up a particular instrument, including, for example, particular sample geometries, heights, etc., will alter the properties of the x-ray spectrum and affect the calibration.

Using standards-less EDS analysis, an analysis of a particular mineral sample is made without comparing to known standards. Based on characteristics of the spectrum collected, such as peaks and emissions at certain energies, the element list is narrowed and ultimately an element is selected. Standards-less analysis is far more complex and subject to greater inaccuracies than standards-based analysis, but it provides for easy setup for the user because it does not require calibrating the instrument using certain parameters for all possible elements.

Accordingly, what is needed is an efficient calibration method and apparatus that is less costly, simpler and easier to implement, and that allows samples to be measured much more rapidly.

SUMMARY OF THE INVENTION

An object of the invention is to provide a method and system for determining the composition of an unknown sample.

The present invention comprises a method for determining the composition of an unknown sample and includes calibrating an x-ray spectrometer in a manner that does not require measuring all possible elements under the operating conditions used to measure an unknown sample to be analyzed. According to a preferred embodiment of the present invention, an x-ray spectrum of an elemental standard is obtained on a particular instrument under operating conditions. The measurement of the spectrum is compared to a previously obtained high quality library spectrum of the same material. A relationship between the library spectrum and the field spectrum is determined. The relationship is then applied to other, previously obtained high quality library spectra to produce a calibrated spectra library that includes calibrated spectra corresponding to other elements in the original library. An unknown sample is then measured and compared to the calibrated spectra library to determine the elements present in the unknown sample. The relationship between the library and the calibrated library can be obtained by measuring a single elemental standard or more than one elemental standard.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings.

The accompanying drawings are not intended to be drawn to scale. In the drawings, each identical or nearly identical component that is illustrated in various figures is represented by a like numeral. For purposes of clarity, not every component may be labeled in every drawing.

DETAILED DESCRIPTION OF PREFERRED EMBODIMENTS

Preferred embodiments of the present invention provide a method for calibrating a local EDS instrument from an x-ray spectrum of a single elemental standard. Preferably, the local EDS instrument will have a stored library containing high quality spectra for all elements being analyzed. The analysis of the single element on the local instrument can be compared to the library spectra for that element, and the comparison used to define a transformation that is used to create a calibrated spectra library that includes a calibrated spectrum for each spectrum in the original library. As a result, the calibration library spectra are much closer to the spectra that would be produced if the calibration standards had been analyzed on the same local instrument using the same instrument set-up. The spectra generated by the local EDS instrument can then be compared to the adjusted library spectra to determine elements in an unknown mineral. In preferred embodiments, this serves to greatly increase the accuracy of elemental identification. In other embodiments multiple elements could be used for calibrating a local EDS instrument, but using only one element is preferable as this decreases the time necessary to establish the calibration.

Figure 1A:
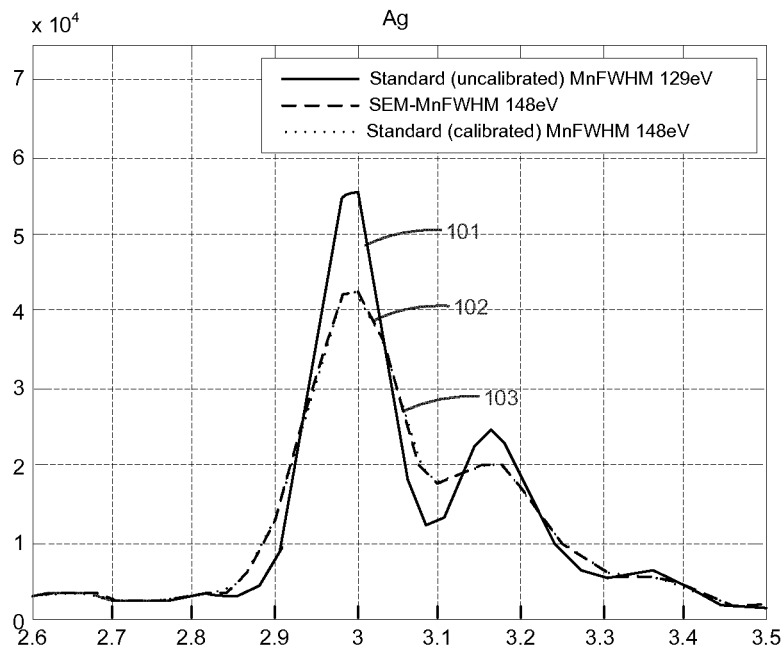
FIG. 1A is a graph of the spectrums of the standards.

FIG. 1A shows the high resolution spectrum of silver, a typical spectrum of silver from a machine in use in the field, and a modified library spectrum, referred to as a calibrated spectrum. Line 101 represents the high resolution standard spectrum for silver that is measured, for example, by a manufacturer and supplied to the user. Line 102 represents a silver spectrum measured on a user's instrument. Line 103 is the "calibrated" silver standard spectrum that was modified from spectrum 101 to match the energy resolution of measured spectrum 102. The peaks match very closely, and the background Bremsstrahlung also matches. In the scale of FIG. 1A, line 102 is indistinguishable from line 103.

Figure 1B:
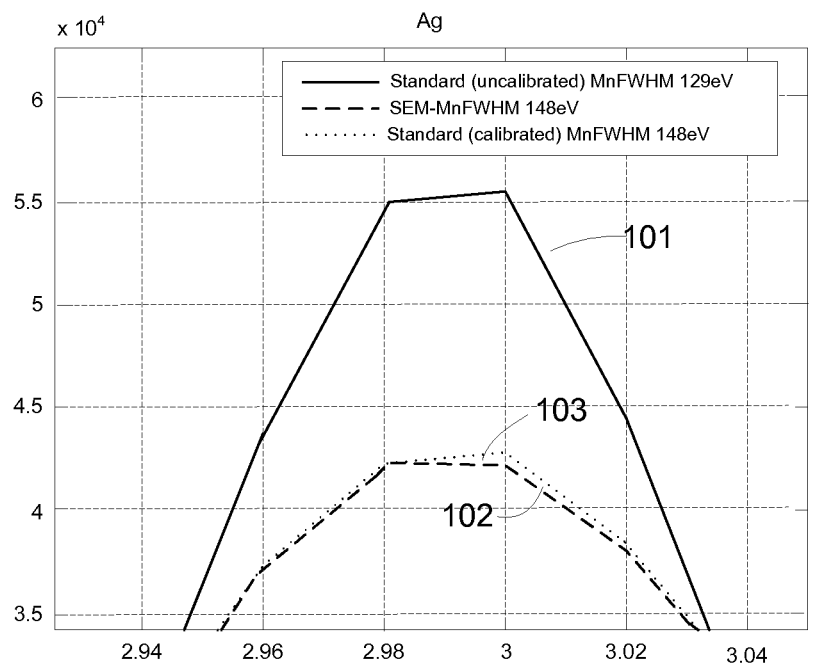
FIG. 1B is a magnified image of FIG. 1A showing that the calibrated spectrum closely matches the measured spectrum.

FIG. 1B is an enlargement showing that the high resolution spectrum represented by line 101 is different from the lower resolution spectrum measured on the user's instrument in line 102, but the lower resolution spectrum measured on the user's instrument of line 102 is very similar to the calibrated spectrum in line 103.

In the prior art QemScan application, x-ray spectra for the 72 elements in a mineral analysis are collected using custom hardware with a fast x-ray pulse processing to acquire the x-ray spectra very quickly. Consequently, the energy resolution of those x-ray spectra is poor. For example, a typical manganese (Mn) full-width half-maximum value is about 170 eV during QemScan acquisition, compared to about 123 eV for high resolution applications.

In a preferred embodiment of the present invention, the stored library spectra can be generated using an EDS instrument (referred to as the source EDS) using a higher quality analysis than is typically used in a field or customer instrument, such as the prior art QemScan. For example, a high quality calibration spectrum may include 1 million x-ray counts. Preferably, the stored library spectra include all of the elements for which the field instrument will be analyzing.

It is quite difficult to perform any kind of meaningful comparison of x-ray spectra from low-resolution field analysis spectra with the high resolution spectra typically used for an elemental standard database. Applicants have discovered, however, that by comparing the field analysis of one element spectrum with the library database spectrum for that same element, it is possible to determine a "blurring" or "smoothing" algorithm that can convert the high quality library spectra to a broader, adjusted field calibration library for use in comparing to unknown samples. Because the smoothing algorithm is based on a spectrum obtained under actual operating conditions, the adjusted library spectra compensate the library spectra for the actual operating conditions and can be used to match unknown spectra measured under those same conditions.

One smoothing algorithm can be used is "Gaussian smoothing," also known as "Gaussian blur," in which an energy specific Gaussian kernel is convolved with the high resolution spectra to produce a lower resolution spectra. In a Gaussian smoothing, values of a Gaussian function are used to determine a convolution matrix which is applied to the original spectrum. This kernel is re-computed for every energy channel because the standard deviation of the kernel increases monotonically with the energy that this channel represents. The height of the spectrum at each energy value is set to a weighted average of heights of nearby points on the spectrum. The original value of the spectral point receives the heaviest weight (having the highest Gaussian value) and neighboring pixels receive smaller weights as their distance to the original energy value increases. A Gaussian function is determined that provides, when applied to the original library spectrum, the closest approximation to the field measurement of the standard under operating conditions. The coefficients used for this blurring are then applied to the other high resolution library elemental spectra. This allows the high resolution spectra in the library database to be transformed into lower resolution spectra that can be more accurately matched with the lower resolution x-ray spectra produced by the field instrument. This process thus provides a spectra database that simulates spectra that would have been acquired if an entire set of calibration standards had been acquired by the field instrument. There are many types of smoothing functions, such as moving average, low pass filter, exponential smoothing, and other types of smoothing functions that may be used in different embodiments.

Figure 2:
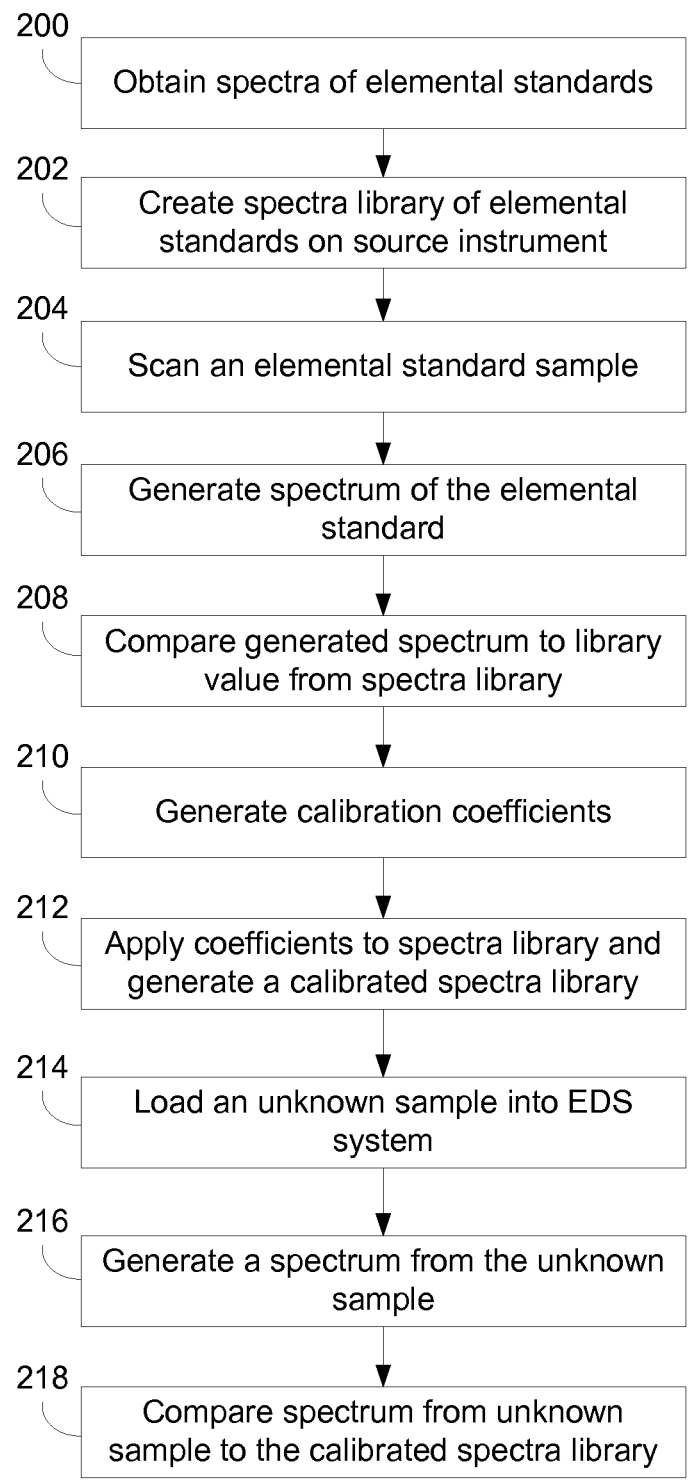
FIG. 2 is a flowchart of steps of a method of standards based calibration according to preferred embodiments of the present invention.

FIG. 2 is a flowchart showing the steps of a preferred embodiment of the present invention. In Step 200, an electron beam system with an x-ray detector obtains high resolution spectra of elemental standards, for example, of the 72 elemental standards. Typically, the spectra of elemental standards are acquired using a high-resolution instrument spectrometer and 1,000,000 x-ray counts per spectrum. In step 202, a spectra library is created from the spectra created in Step 200. The spectra library can be stored, for example, in a database. In Step 204, the field electron beam system with x-ray detector scans an elemental standard sample, for example, a sample of pure copper. Copper is an especially good choice for the local calibration standard because it has two significant x-ray peaks that have a reasonably good response over a wide range of electron energies, and copper is typically present in the sample holder of an EDS instrument. The electron beam can thus be directed at the sample holder itself instead of requiring a separate calibration standard to be loaded into the instrument. Typically, the resolution of the spectra from the field electron beam system is more coarse than the resolution of the library spectra of elemental standards, which are typically generated in a factory setting with a finer resolution energy detector and more x-ray counts.

In step 206 a spectrum of the elemental standard sample is generated. In step 208 the generated spectrum is compared to a library value from the spectra library for the same element. For example, if copper is used as the local calibration standard, the spectra from the copper calibration would be compared to the library value for copper. In step 210 calibration coefficients are determined that, when used in a smoothing function applied to the library spectrum, will produce the generated spectrum. The calibration coefficients could be, for example, the coefficients of a Gaussian blurring function. In step 212, the smoothing algorithm with the coefficients determined in step 210 is applied to the library spectra to generate a calibrated spectra library. In step 214 an unknown sample is loaded into the EDS customer machine. In step 216, the electron beam is directed to a sample of unknown composition to generate a spectrum. In step 218, the spectrum of the unknown sample is compared to the calibrated database spectra to determine elemental composition of unknown sample through elemental decomposition. The unknown sample can be determined, for example, by calculating a similarity metric between the spectrum of the unknown spectrum and each element of the modified library spectra, and then selecting the closest match. For example, the similarity metric may sum the squares of the differences between the two spectra at each energy range. The unknown element is presumed to be the element who's modified library spectrum is the closest match to the spectrum of the unknown sample.

Figure 3:
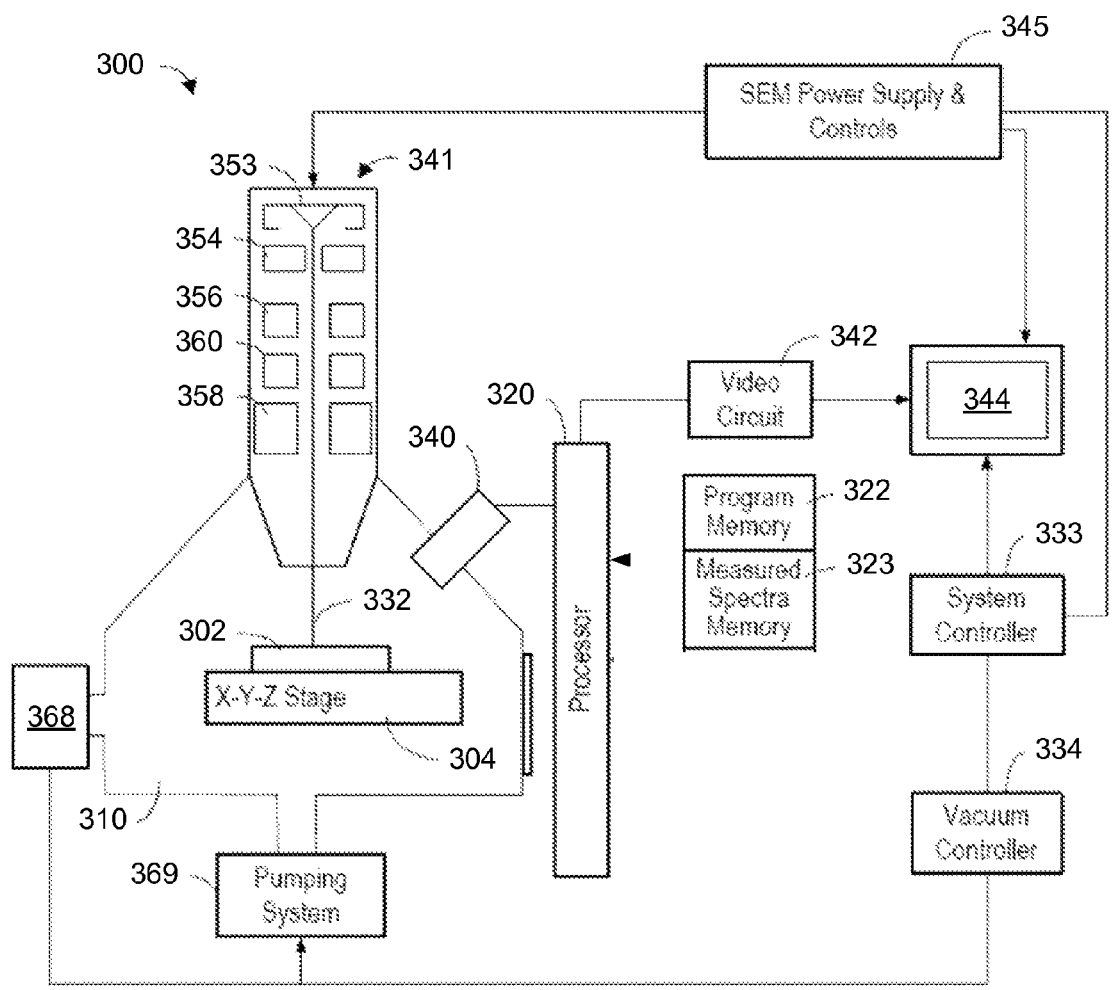
FIG. 3 shows a scanning electron beam with an x-ray detector suitable for analyzing standards according to preferred embodiments of the present invention.

FIG. 3 shows an example of a scanning electron beam system 300 with an x-ray detector 340 suitable for analyzing samples prepared according to the present invention. A scanning electron microscope 341, along with power supply and control unit 345, is provided with system 300. An electron beam 332 is emitted from a cathode 353 by applying voltage between cathode 353 and an anode 354. Electron beam 332 is focused to a fine spot by means of a condensing lens 356 and an objective lens 358. Electron beam 332 is scanned two-dimensionally on the specimen by means of a deflection coil 360. Operation of condensing lens 356, objective lens 358, and deflection coil 360 is controlled by power supply and control unit 345.

A system controller 333 controls the operations of the various parts of scanning electron beam system 300. The vacuum chamber 310 is evacuated with ion pump 368 and mechanical pumping system 369 under the control of vacuum controller 334.

Electron beam 332 can be focused onto sample 302, which is on movable X-Y stage 304 within lower vacuum chamber 310. When the electrons in the electron beam strike sample 302, the sample gives off x-rays whose energy correlated to the elements in the sample. X-rays having energy inherent to the elemental composition of the sample are produced in the vicinity of the electron beam incident region. Emitted x-rays are collected by x-ray detector 340, preferably an energy dispersive detector of the silicon drift detector type, although other types of detectors could be employed, which generates a signal having an amplitude proportional to the energy of the detected x-ray.

Output from detector 340 is amplified and sorted by the processor 320, which counts and sorts the total number of x-rays detected during a specified period of time, at a selected energy and energy resolution, and a channel width (energy range) of typically between 2.5 and 20 eV per channel. Processor 320 can comprise a computer processor; operator interface means (such as a keyboard or computer mouse); program memory 322 for storing data and executable instructions; interface means for data input and output, executable software instructions embodied in executable computer program code; and display 344 for displaying the results of a multivariate spectral analysis by way of video circuit 342.

Processor 320 can be a part of a standard laboratory personal computer, and is typically coupled to at least some form of computer-readable media. Computer-readable media, which include both volatile and nonvolatile media, removable and non-removable media, may be any available medium that can be accessed by processor 320. By way of example and not limitation, computer-readable media comprise computer storage media and communication media. Computer storage media include volatile and nonvolatile, removable and non-removable media implemented in any method or technology for storage of information such as computer-readable instructions, data structures, program modules or other data. For example, computer storage media include RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by processor 320.

Program memory 322 can include computer storage media in the form of removable and/or non-removable, volatile and/or nonvolatile memory and can provide storage of computer-readable instructions, data structures, program modules and other data. Generally, the processor 320 is programmed by means of instructions stored at different times in the various computer-readable storage media of the computer. Programs and operating systems are typically distributed, for example, on floppy disks or CD-ROMs. From there, they are installed or loaded into the secondary memory of a computer. At execution, they are loaded at least partially into the computer's primary electronic memory. The invention described herein includes these and other various types of computer-readable storage media when such media contain instructions or programs for implementing the steps described below in conjunction with a microprocessor or other data processor. The invention also includes the computer itself when programmed according to the methods and techniques described herein.

An x-ray spectrum obtained as described above can be stored in a portion of memory 322, such as the measured spectra memory portion 323. Elemental standards are also stored in measured spectra memory 323.

While the embodiment shown includes a scanning electron microscope, related embodiment could use a transmission electron microscope or a scanning transmission electron microscope to generate x-rays from the sample. An x-ray fluorescence system could also be used to generate x-rays from the sample. Other embodiments may detect other characteristic radiation, such as gamma rays, from a sample.

A preferred method or apparatus of the present invention has many novel aspects, and because the invention can be embodied in different methods or apparatuses for different purposes, not every aspect need be present in every embodiment. Moreover, many of the aspects of the described embodiments may be separately patentable. The invention has broad applicability and can provide many benefits as described and shown in the examples above. The embodiments will vary greatly depending upon the specific application, and not every embodiment will provide all of the benefits and meet all of the objectives that are achievable by the invention.

It should be recognized that embodiments of the present invention can be implemented via computer hardware, a combination of both hardware and software, or by computer instructions stored in a non-transitory computer-readable memory. The methods can be implemented in computer programs using standard programming techniques—including a non-transitory computer-readable storage medium configured with a computer program, where the storage medium so configured causes a computer to operate in a specific and predefined manner—according to the methods and figures described in this Specification. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits programmed for that purpose.

Further, methodologies may be implemented in any type of computing platform, including but not limited to, personal computers, mini-computers, main-frames, workstations, networked or distributed computing environments, computer platforms separate, integral to, or in communication with charged particle tools or other imaging devices, and the like. Aspects of the present invention may be implemented in machine readable code stored on a non-transitory storage medium or device, whether removable or integral to the computing platform, such as a hard disc, optical read and/or write storage mediums, RAM, ROM, and the like, so that it is readable by a programmable computer, for configuring and operating the computer when the storage media or device is read by the computer to perform the procedures described herein. Moreover, machine-readable code, or portions thereof, may be transmitted over a wired or wireless network. The invention described herein includes these and other various types of non-transitory computer-readable storage media when such media contain instructions or programs for implementing the steps described above in conjunction with a microprocessor or other data processor. The invention also includes the computer itself when programmed according to the methods and techniques described herein.

Computer programs can be applied to input data to perform the functions described herein and thereby transform the input data to generate output data. The output information is applied to one or more output devices such as a display monitor. In preferred embodiments of the present invention, the transformed data represents physical and tangible objects, including producing a particular visual depiction of the physical and tangible objects on a display.

While the examples provided above describe the use of the present invention to prepare samples for EDS analysis, the invention can also be used to prepare samples for other types of analysis, including wavelength dispersive spectroscopy (WDS), x-ray diffraction (XRD), or x-ray fluorescence (XFR). Also, while the embodiments above use a single calibration standard to determine the transformation, other embodiments use multiple calibration standards to produce a more accurate transformation.

Although much of the previous description is directed at mineral samples from drill cuttings, the invention could be used to prepare samples of any suitable material. The terms "work piece," "sample," "substrate," and "specimen" are used interchangeably in this application unless otherwise indicated. Further, whenever the terms "automatic," "automated," or similar terms are used herein, those terms will be understood to include manual initiation of the automatic or automated process or step.

In the following discussion and in the claims, the terms "including" and "comprising" are used in an open-ended fashion, and thus should be interpreted to mean "including, but not limited to . . . . " To the extent that any term is not specially defined in this specification, the intent is that the term is to be given its plain and ordinary meaning. The accompanying drawings are intended to aid in understanding the present invention and, unless otherwise indicated, are not drawn to scale. Particle beam systems suitable for carrying out the present invention are commercially available, for example, from FEI Company, the assignee of the present application.

Although the present invention and its advantages have been described in detail, it should be understood that various changes, substitutions and alterations can be made to the embodiments described herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method of performing energy-dispersive x-ray spectroscopy, comprising:
    creating, using a source instrument, library spectra by:
        directing, using an electron source and focusing options of the source instrument, an electron beam toward one or more elemental standards;
        obtaining, using a x-ray detector of the source instrument, energy-dispersive x-ray spectra of the one or more elemental standards;
        creating a spectra library from the spectra of the one or more elemental standards;
    creating, using a field instrument, calibration spectra, the calibration spectra having a lower resolution than the library spectra by:
        directing, using an electron source and focusing options of the field instrument, an electron beam toward an elemental standard sample;
        obtaining, using an x-ray detector of the field instrument, an energy-dispersive x-ray spectrum of the elemental standard sample;
        comparing the spectrum of the elemental standard sample to an elemental standard of the spectra library;
        determining a transformation based on the comparison of the spectrum of the elemental standard sample to the elemental standard of the spectra library;
        applying the transformation to the spectra library to generate a calibrated spectra library;
    determining, using the field instrument, the elements in an unknown mineral sample, the unknown mineral sample comprising a sample of unknown mineral composition, by:
        directing, using an electron source and focusing options of the field instrument, an electron beam toward the unknown mineral sample;
        obtaining, using the x-ray detector of the field instrument, an energy-dispersive x-ray spectrum of the unknown mineral sample; and
        comparing the obtained spectrum of the unknown mineral sample to the calibrated spectra library.

2. The method of claim 1, in which determining the transformation includes determining coefficients for a smoothing function.

3. The method of claim 1, in which applying the transformation includes applying a smoothing function.

4. The method of claim 3 in which applying the smoothing function includes applying a Gaussian smoothing function.

5. The method of claim 1, further comprising storing the library spectra in a database.

6. The method of claim 1 in which applying the transformation to the spectra library includes applying a Gaussian blur to the spectra library.

7. The method of claim 1 further comprising determining elemental composition of the unknown sample through elemental decomposition based on the comparison of the generated spectrum of the unknown mineral sample to the calibrated sample library.

8. The method of claim 1 in which obtaining spectra of elemental standards includes obtaining spectra of elemental standards in a high resolution instrument in which at least one million x-ray counts are detected.

9. The method of claim 1 in which scanning an elemental standard sample includes scanning an elemental standard sample with an instrument of lower resolution than the high resolution instrument for obtaining the spectra of elemental standards.

10. The method of claim 1 in which obtaining a spectra of elemental standard and scanning an elemental standard sample are performed on different mineral analysis instruments.

11. The method of claim 1 in which obtaining spectra of elemental standards includes obtaining spectra of all 72 elements in mineral analysis.

12. The method of claim 1 in which scanning an elemental standard includes scanning copper.

13. The method of claim 1 in which scanning an elemental standard includes scanning a sample holder.

14. The method of claim 1, further comprising identifying the unknown mineral sample.

15. A method of calibrating an instrument for mineral analysis, comprising:
    scanning, using an electron beam of the instrument, an elemental standard sample;
    obtaining, using an x-ray detector of the instrument, an energy-dispersive x-ray spectrum of the elemental standard sample;
    comparing the obtained spectrum of the elemental standard sample to a library value of a library of elemental standard spectra in which the library value has higher resolution than the obtained spectrum of the elemental standard sample;
    generating calibration coefficients from the comparison of the obtained spectrum of the elemental standard sample to the library value; and
    applying the calibration coefficients to the library of elemental standard spectra to generate a calibrated library of elemental standard spectra.

16. The method of claim 15 in which applying the calibration coefficients to the library of elemental standard spectra includes applying a Gaussian blur to the elemental standard spectra.

17. The method of claim 15 in which the library of elemental standard spectra is obtained on an instrument different from the instrument being calibrated.

18. The method of claim 15 in which the library of elemental standard spectra includes spectra from 72 minerals for mineral analysis.

19. The method of claim 15 further comprising:
    loading an unknown mineral sample into the instrument;
    generating an unknown sample spectrum;
    comparing the generated unknown sample spectrum to the calibrated library of elemental standard spectra; and
    determining elemental composition of the unknown sample.

20. A system for determining composition of an unknown sample, comprising:

a source of electrons for forming an electron beam;
focusing optics for focusing a beam of electrons onto a sample;
an x-ray detector for detecting x-rays emitted from the sample upon impact of the electron beam;
a computer readable memory storing:
   library x-ray spectra corresponding to multiple elements;
   computer instructions for:
      comparing a spectrum acquired from a known element with a library x-ray spectrum of the known element in which the library x-ray spectrum of the known element has a higher resolution than the spectrum acquired from the known element;
      determining a transformation between the spectrum acquired from the known element and the library spectrum of the known element;
      applying the transformation to all spectra of the library x-ray spectra to determine calibration spectra;
      comparing a spectrum of a material of an unknown composition to the calibration spectra to determine the composition of the unknown material.

* * * * *